(12) United States Patent
Shih

(10) Patent No.: US 9,993,320 B2
(45) Date of Patent: Jun. 12, 2018

(54) COMB-SHAPED TOOTHPICK STRUCTURE AND METHOD FOR MANUFACTURING SAME

(71) Applicant: Ting-Ting Shih, Nantou (TW)

(72) Inventor: Ting-Ting Shih, Nantou (TW)

( * ) Notice: Subject to any disclaimer, the term of this patent is extended or adjusted under 35 U.S.C. 154(b) by 152 days.

(21) Appl. No.: 15/073,869

(22) Filed: Mar. 18, 2016

(65) Prior Publication Data
US 2017/0265976 A1 Sep. 21, 2017

(51) Int. Cl.
*A61C 15/02* (2006.01)
*B26D 3/08* (2006.01)

(52) U.S. Cl.
CPC .......... *A61C 15/02* (2013.01); *B26D 3/08* (2013.01); *Y10T 29/5176* (2015.01)

(58) Field of Classification Search
CPC .................. A61C 15/02; Y10T 29/5176
USPC ...... 132/321, 322, 323, 324, 325, 326, 327, 132/328, 329; 29/56.5
See application file for complete search history.

(56) References Cited

U.S. PATENT DOCUMENTS

| | | | | |
|---|---|---|---|---|
| 3,563,253 A | * | 2/1971 | Barman | A61C 15/02 132/329 |
| 4,660,583 A | * | 4/1987 | Brown | A61C 15/02 132/329 |
| 8,177,553 B2 | * | 5/2012 | Stoll | A61C 5/85 132/329 |

FOREIGN PATENT DOCUMENTS

| | | | | |
|---|---|---|---|---|
| FR | 1269529 A | * | 8/1961 | A61C 15/02 |
| FR | 1474536 A | * | 3/1967 | A61C 15/02 |
| TW | M304327 U | | 1/2007 | |

* cited by examiner

*Primary Examiner* — Sunil K Singh
*Assistant Examiner* — Michael Vitale
(74) *Attorney, Agent, or Firm* — Muncy, Geissler, Olds & Lowe, P.C.

(57) ABSTRACT

A method for manufacturing a comb-shaped toothpick structure includes cutting a wooden block by a rotary cutter having a plurality of dies to form a plurality of toothpick shapes arranged in a row. Each toothpick shape includes a top edge formed by a cutter groove between two dies. Each toothpick shape further includes at least one stepped portion formed by at least one stepped cutting portion of one of the dies. The bottoms of the toothpick shapes are connected to each other. A bottom groove is located between two adjacent toothpick shapes and is formed by a blade of one of the dies. The toothpick shapes is further cut by partial cutting at an end of the toothpick shapes to form a front end of each toothpick shape. The toothpick shapes are cut from the wooden block to obtain a toothpick structure including a plurality of toothpicks.

6 Claims, 9 Drawing Sheets

PRIOR ART

COMB-SHAPED TOOTHPICK STRUCTURE AND METHOD FOR MANUFACTURING SAME

BACKGROUND OF THE INVENTION

The present invention relates to a toothpick structure and a method for manufacturing the toothpick structure and, more particularly, to a comb-shaped toothpick structure and a method for manufacturing the comb-shaped toothpick structure.

FIG. 1 shows a conventional comb-shaped toothpick structure, an example of which is shown in Taiwan Utility Model No. M304327. The conventional comb-shaped toothpick structure includes a row of toothpicks 60 connected with each other. The toothpicks 60 can be separated from each other for use. Each toothpick 60 includes a grip section 61 and a tooth picking section 62 at a front end thereof. The bottoms of the row of toothpicks 60 are continuously connected during formation of the toothpicks 60. When in use, a toothpick 60 is separated from the row of toothpicks 60. Each toothpick 60 includes a sharp top edge 601; namely, the toothpick 60 tapers upwards. However, the toothpick 60 having two smooth, arcuate, outer sides providing insufficient structural strength, such that the toothpick 60 is apt to break.

Furthermore, only the tooth picking section 62 at the front end of the toothpick 60 can be used to remove food residue from the teeth. The food residue stuck on the gum surfaces can only be removed by repeatedly using the tooth picking section 62, leading to the risk of injury to the oral epidermis by the sharp tooth picking section 62, because the two sides of the toothpick 60 have no provisions for contacting with the surfaces of the teeth while using the toothpick 60.

Furthermore, the two smooth sides of the toothpick 60 have insufficient strength, such that the user would feel the toothpick 60 is too soft and, thus, could not exert a sufficient force for removing the food residue. As a result, the toothpick 60 of this type provides convenient use, but the utility is poor.

BRIEF SUMMARY OF THE INVENTION

A method for manufacturing a comb-shaped toothpick structure according to the present invention includes a first formation step including positioning a wooden block by a positioning device, moving the wooden block to a cutting position, and cutting the wooden block by a rotary cutter. The rotary cutter includes a plurality of dies on a surface thereof. Each of the plurality of dies includes a top end having a blade. Each of the plurality of dies includes two sides. Each of the two sides of each of the plurality of dies includes an intermediate portion having at least one stepped cutting portion. A cutter groove is defined in a connection area between two adjacent dies. The wooden block is cut by the rotary cutter to form a plurality of toothpick shapes arranged in a row. Each of the plurality of toothpick shapes includes a top edge formed by the cutter groove. Each of the plurality of toothpick shapes further includes at least one stepped portion formed by the at least one stepped cutting portion. Each of the plurality of toothpick shapes further includes a bottom. The bottoms of the plurality of toothpick shapes are connected to each other. A bottom groove is located between two adjacent toothpick shapes and is formed by the blade. The method further includes a second formation step including partially cutting the plurality of toothpick shapes beginning from a start location spaced from an end of the plurality of toothpick shapes towards the end of the plurality of toothpick shapes. The partial cutting in the second formation step is carried out along a slope or a curve to cut two sides of the top edge, two sides of the at least one stepped portion, and two sides of the bottom groove of each of the plurality of toothpick shapes to form a front end of each of the plurality of toothpick shapes. The method further includes a cutting step including cutting the plurality of toothpick shapes from the wooden block along a cutting line to obtain a toothpick structure including a plurality of toothpicks. A spacing between the top edge of each of the plurality of toothpick shapes and the cutting line is larger than a depth from the top edge of each of the plurality of toothpick shapes and the bottom groove.

The positioning device can include a pressing rod and an actuation face. The pressing rod can be controlled to position the wooden block on the actuation face. The actuation face moves the wooden block positioned thereon to the cutting position.

In an example, the at least one stepped portion includes first, second, and third stepped portions formed on of each of two sides of each of the plurality of toothpicks. Each of the first, second, and third stepped portions on one of the two sides of each of the plurality of toothpicks includes a first lateral edge. Each of the first, second, and third stepped portions on the other side of each of the plurality of toothpicks includes a second lateral edge. The first lateral edges of the first, second, and third stepped portions on the one of the two sides of each of the plurality of toothpicks are located on a first plane. The second lateral edges of the first, second, and third stepped portions on the other side of each of the plurality of toothpicks are located on a second plane.

The partial cutting in the second formation step can include using the rotary cutter to cut the two sides of the top edge, the two sides of the at least one stepped portion, and the two sides of the bottom groove of each of the plurality of toothpick shapes to form the front end of each of the plurality of toothpick shapes.

Each of the plurality of toothpicks includes a longitudinal plane passing through the top edge and a central portion of the bottom. An angle between the longitudinal plane and each of the first and second planes is in a range between 10° and 20°.

The method can further include a polishing step before the cutting step. The polishing step includes controlling a polishing wheel to move along a path of the rotary cutter in the first and second formation steps to polish surfaces of the plurality of toothpick shapes after the first and second formation steps.

A comb-shaped toothpick structure according to the present invention includes a plurality of toothpicks arranged in a row. Each of the plurality of toothpicks includes a top edge, a bottom, and at least one stepped portion between the top edge and the bottom. The bottoms of the plurality of toothpicks are connected to each other. A bottom groove is defined between two adjacent toothpicks and is configured to permit separation of the two adjacent toothpicks.

In an example, the at least one stepped portion includes first, second, and third stepped portions formed on each of two sides of each of the plurality of toothpicks. Each of the first, second, and third stepped portions on one of the two sides of each of the plurality of toothpicks includes a first lateral edge. Each of the first, second, and third stepped portions on the other side of each of the plurality of toothpicks includes a second lateral edge. The first lateral edges of the first, second, and third stepped portions on the one of the two sides of each of the plurality of toothpicks are located on a first plane. The second lateral edges of the first, second, and third stepped portions on the other side of each of the plurality of toothpicks are located on a second plane.

Each of the plurality of toothpicks includes a longitudinal plane passing through the top edge and a central portion of the bottom. An angle between the longitudinal plane and each of the first and second planes is in a range between 10° and 20°.

The present invention will become clearer in light of the following detailed description of illustrative embodiments of this invention described in connection with the drawings.

DETAILED DESCRIPTION OF THE INVENTION

Figure 1:
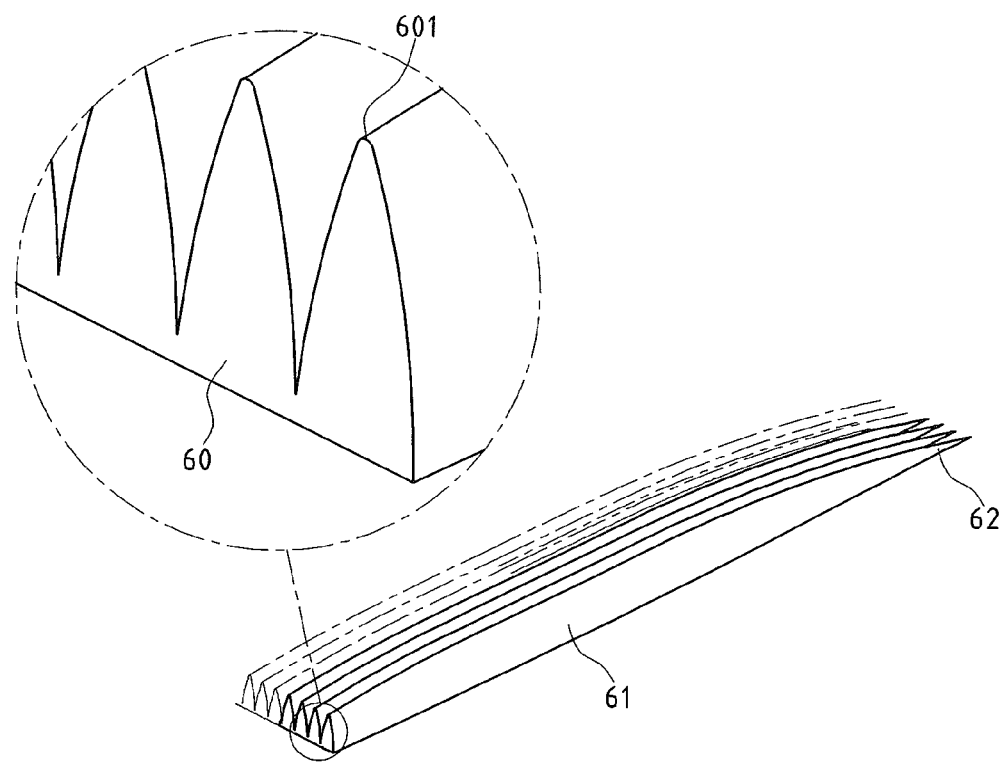
FIG. 1 is a perspective view of a comb-shaped toothpick structure.
Figure 2:
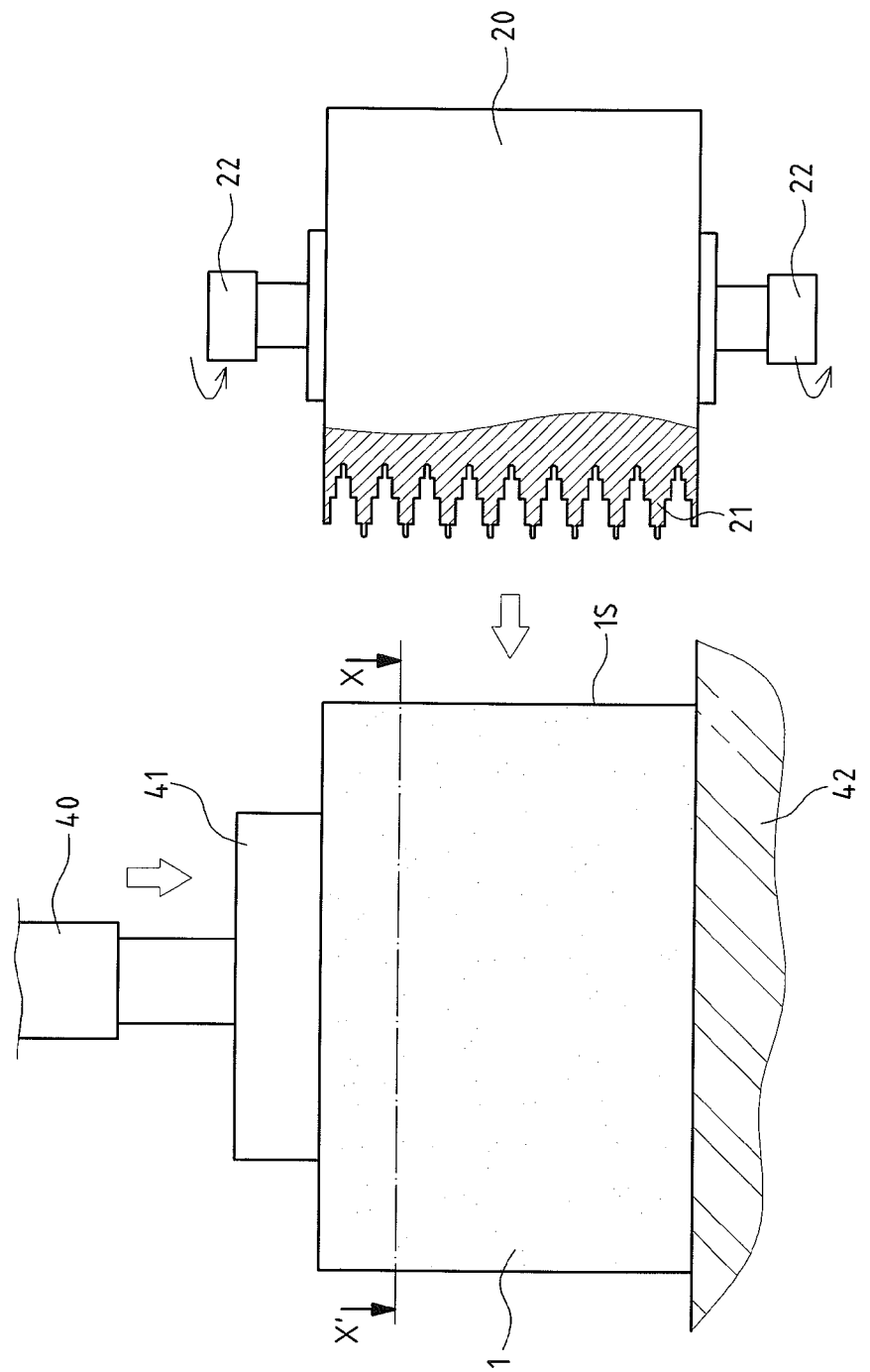
FIG. 2 is a diagrammatic view illustrating a positioning device for positioning a wooden block to be processed and a rotary cutter for processing the wooden block to form a comb-shaped toothpick structure according to the present invention.

With reference to FIG. 2, a method for manufacturing a comb-shaped toothpick structure of an example according to the present invention includes a first formation step. Specifically, the first formation step includes positioning a wooden block 1 by a positioning device 40, moving the wooden block 1 to a cutting position, and cutting the wooden block 1 by a rotary cutter 20. In an example, the positioning device 40 includes a pressing rod 41 and an actuation face 42. The pressing rod 41 can be controlled (such as by a mechanical provision) to position the wooden block 1 on the actuation face 42. The actuation face 42 moves the wooden block 1 positioned thereon to the cutting position. A face 1S of the wooden block 1 can be cut by the rotary cutter 20.

Figure 3:
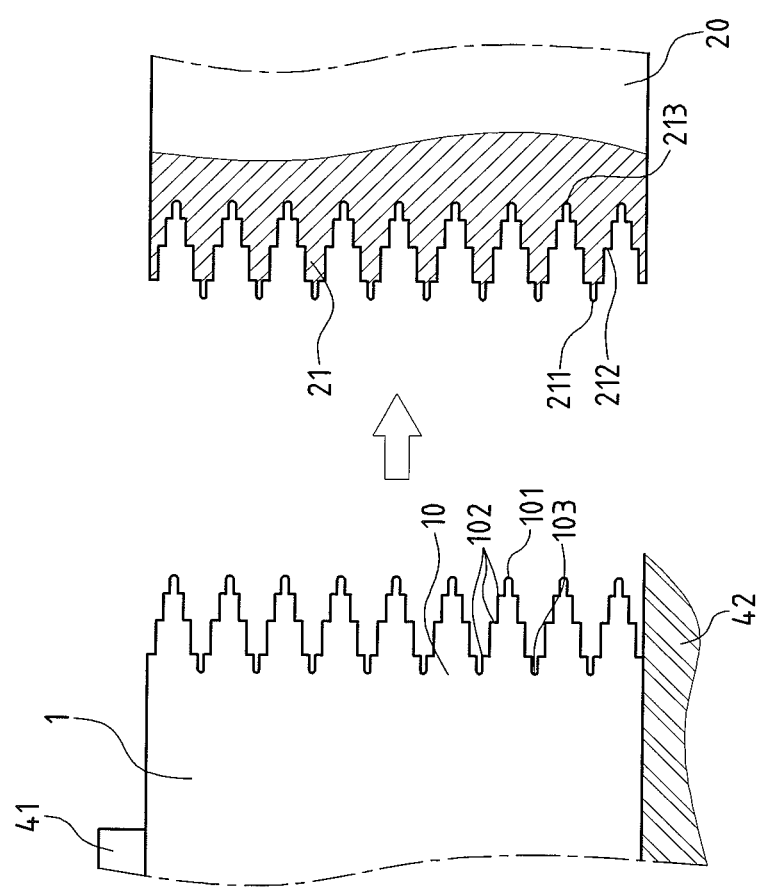
FIG. 3 is a diagrammatic view illustrating a first formation step for forming the comb-shaped toothpick structure according to the present invention.

With reference to FIGS. 2 and 3, in an example, the rotary cutter 20 includes a plurality of dies 21 arranged in a row on a surface thereof. Each die 21 includes a top end having a blade 211. Each of two sides of each die 21 includes an intermediate portion having at least one stepped cutting portion 212. A cutter groove 213 is defined in a connection area between two adjacent dies 21. In this example, the intermediate portion of each of the two sides of each die 21 includes first, second, and third stepped cutting portions 212.

The face 1S of the wooden block 1 is cut by the rotary cutter 20 to form a plurality of toothpick shapes 10 arranged in a row. Each toothpick shape 10 has an outline similar to a toothpick. Each toothpick shape 10 includes a top edge 101 formed by the cutter groove 213. Each toothpick shape 10 further includes at least one stepped portion 102 formed by the at least one stepped cutting portion 212. Each toothpick shape 10 further includes a bottom. The bottoms of the toothpick shapes 10 are connected to each other. A bottom groove 103 is located between two adjacent toothpick shapes 10 and is formed by the blade 211. The length of the rolling cutting path of the rotary cutter 20 acting on the face 1S is equal to the length of each toothpick shape 10. The movement of the rotary cutter 20 is controlled by an external power device through a driving shaft 22.

Figure 8:
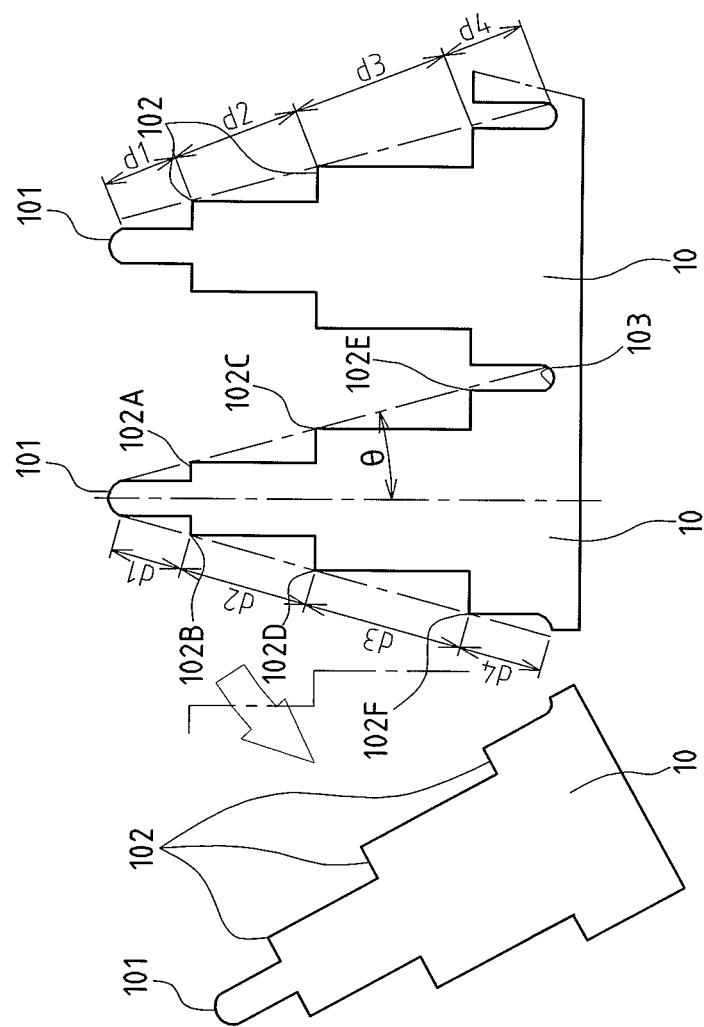
FIG. 8 is a cross sectional view illustrating separation of a toothpick from the comb-shaped toothpick structure.

In the example in which the intermediate portion of each of the two sides of each die 21 includes first, second, and third stepped cutting portions 212, each of the two sides of each toothpick shape 10 includes first, second, and third stepped portions 102. With reference to FIG. 8, each of the first, second, and third stepped portions 102 on one of the two sides of each toothpick shape 10 includes a first lateral edge 102A, 102C, 102E. Each of the first, second, and third stepped portions 102 on the other side of each toothpick shape 10 includes a second lateral edge 102B, 102D, 102F. The first lateral edges 102A, 102C, and 102E of the first, second, and third stepped portions 102 on one of the two sides of each toothpick shape 10 are located on a first plane P1. The second lateral edges 102B, 102D, and 102F of the first, second, and third stepped portions 102 on the other side of each toothpick shape 10 are located on a second plane P2.

A spacing d1 between the top edge 101 and the first lateral edge 102A of the first stepped portion 102 is substantially equal to a spacing d4 between the first lateral edge 102E of the third stepped portion 102 and a bottom wall of a corresponding bottom groove 103. A spacing d2 between the first lateral edge 102A of the first stepped portion 102 and the first lateral edge 102C of the second stepped portion 102 is substantially equal to a spacing d3 between the first lateral edge 102O of the second stepped portion 102 and the first lateral edge 102E of the third stepped portion 102.

A spacing d1 between the top edge 101 and the second lateral edge 102B of the first stepped portion 102 is substantially equal to a spacing d4 between the second lateral edge 102F of the third stepped portion 102 and a bottom wall of a corresponding bottom groove 103. A spacing d2 between the second lateral edge 102B of the first stepped portion 102 and the second lateral edge 102D of the second stepped portion 102 is substantially equal to a spacing d3 between the second lateral edge 102D of the second stepped portion 102 and the second lateral edge 102F of the third stepped portion 102.

Each toothpick shape 10 includes a longitudinal plane L passing through the top edge 101 and a central portion of the bottom. An angle θ between the longitudinal plane L and each of the first and second planes P1 and P2 is in a range between 10° and 20°.

Figure 4:
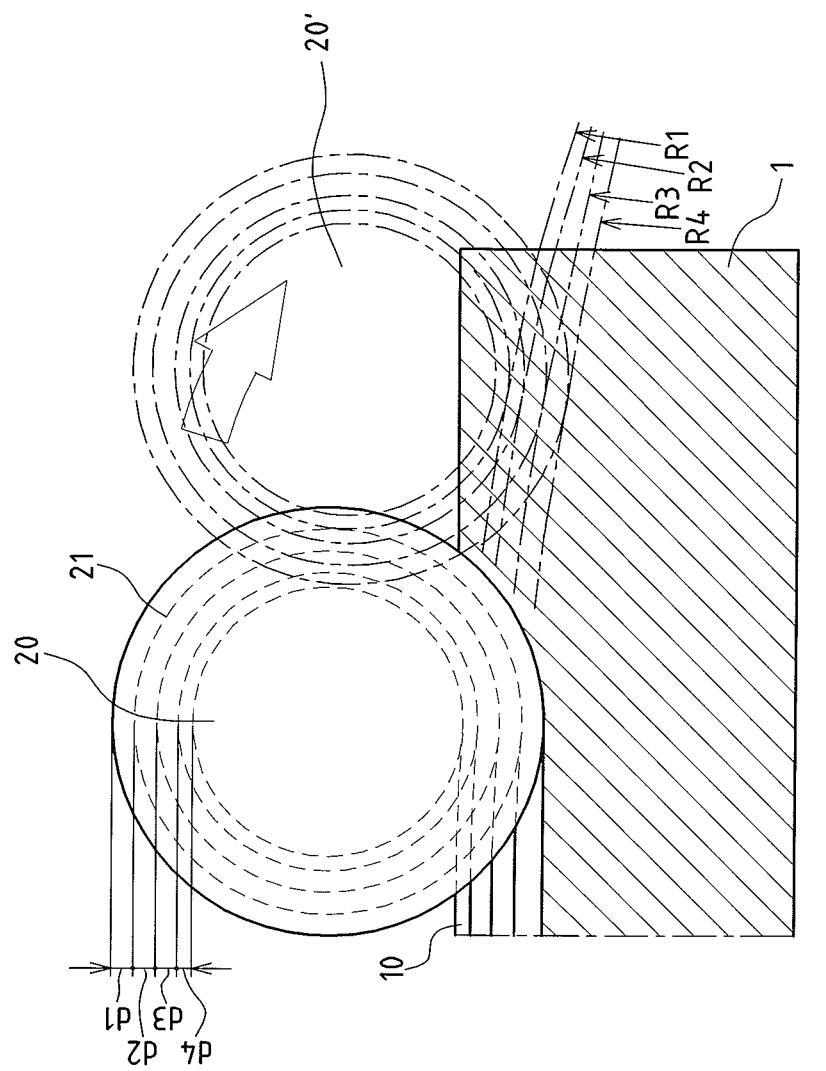
FIG. 4 is a diagrammatic side view illustrating a second formation step of the comb-shaped toothpick structure according to the present invention.

With reference to FIG. 4, the method further includes a second formation step which includes partially cutting the toothpick shapes 10 beginning from a start location spaced from an end of the toothpick shapes 10 towards the end of the toothpick shapes 10. The partial cutting in the second formation step is carried out along a slope or a curve to cut the two sides of the top edge 101, the two sides of the at least one stepped portion 102, and the two sides of the bottom groove 103 of each toothpick shape 101 to form a front end of each toothpick shape 10. An example of the radiuses of curvatures R1, R2, R3, and R4 for cutting and the spacings d1, d2, d3, and d4 are R1, R2, R3, and R4 are shown in FIG.

4 and FIG. 8. The rotary cutter 20 moves from a position indicated by the phantom lines (see rotary cutter 20').

Figure 5:
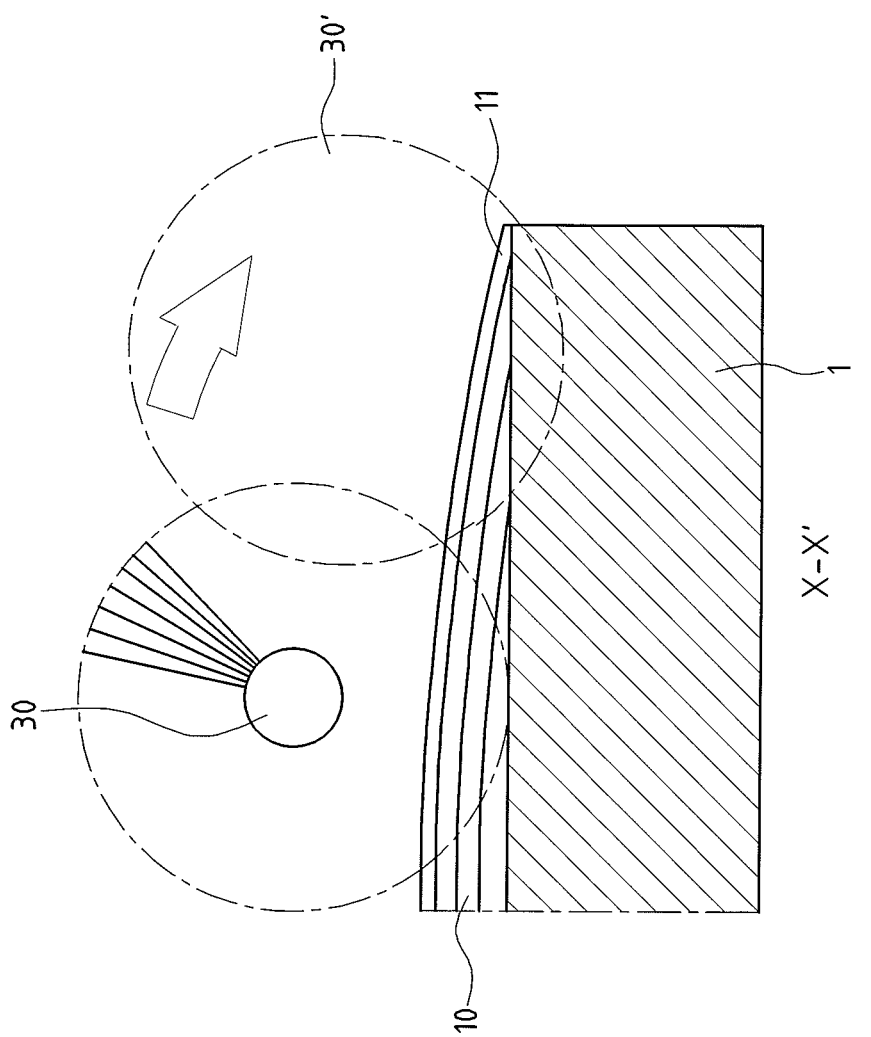
FIG. 5 is a diagrammatic side view illustrating a polishing step of the comb-shaped toothpick structure according to the present invention.

With reference to FIG. 5, the method can further include a polishing step after the second formation step. The polishing step includes controlling a polishing wheel 30 to move along the path of the rotary cutter 20 in the first and second formation steps to polish surfaces of the toothpick shapes 10 after the first and second formation steps. Note that the polishing wheel 30 moves to a position indicated by 30'.

Figure 6:
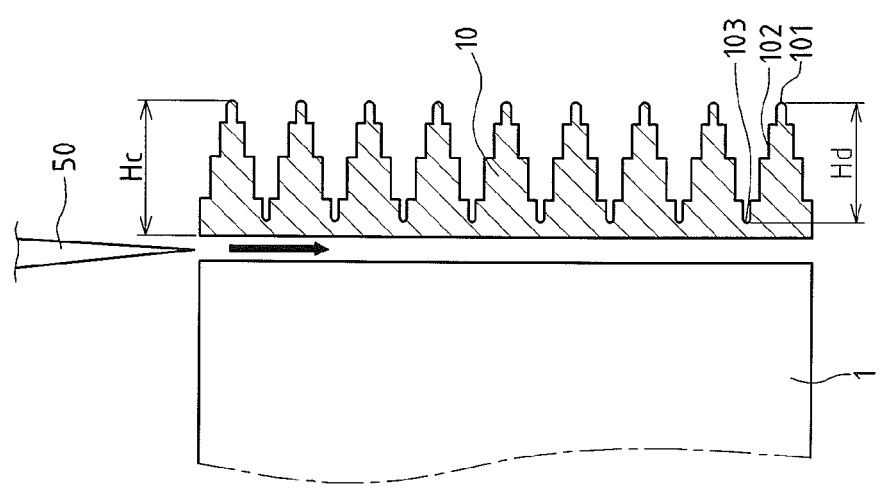
FIG. 6 is a diagrammatic view illustrating a cutting step of the comb-shaped toothpick structure according to the present invention.

With reference to FIG. 6, the method further includes a cutting step including using a cutter 50 to cut the toothpick shapes 10 from the wooden block 1 along a cutting line to thereby obtain a toothpick structure. The resultant toothpick structure includes a plurality of toothpicks (also designated by 10). The rear end of each toothpick 10 is substantially the same as that of the toothpick shape 10 mentioned with reference to FIG. 8. A spacing Hc between the top edge 101 of each toothpick shape 10 and the cutting line is larger than a depth Hd from the top edge 101 of each toothpick shape 101 and the bottom groove 103.

Figure 7:
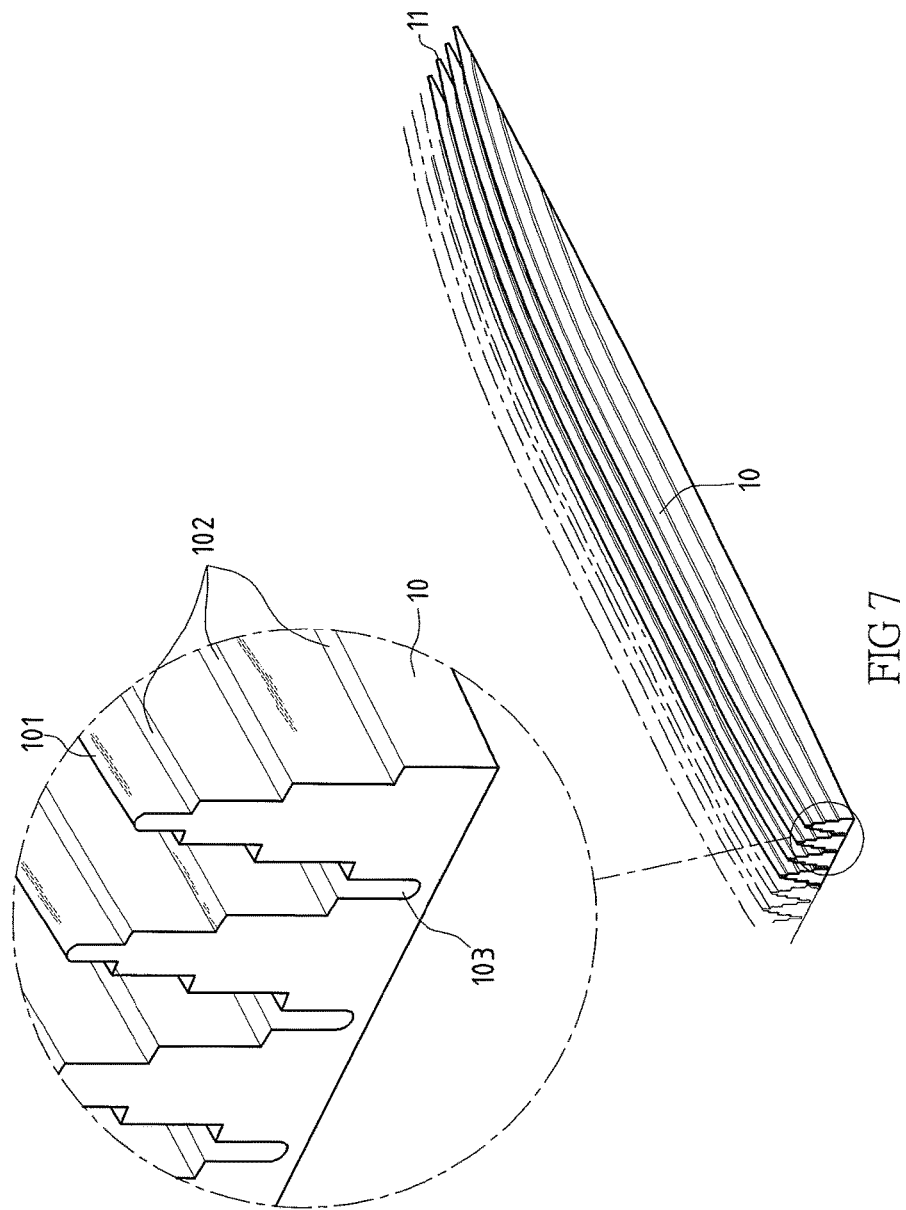
FIG. 7 is a perspective view of the comb-shaped toothpick structure according to the present invention.
Figure 9:
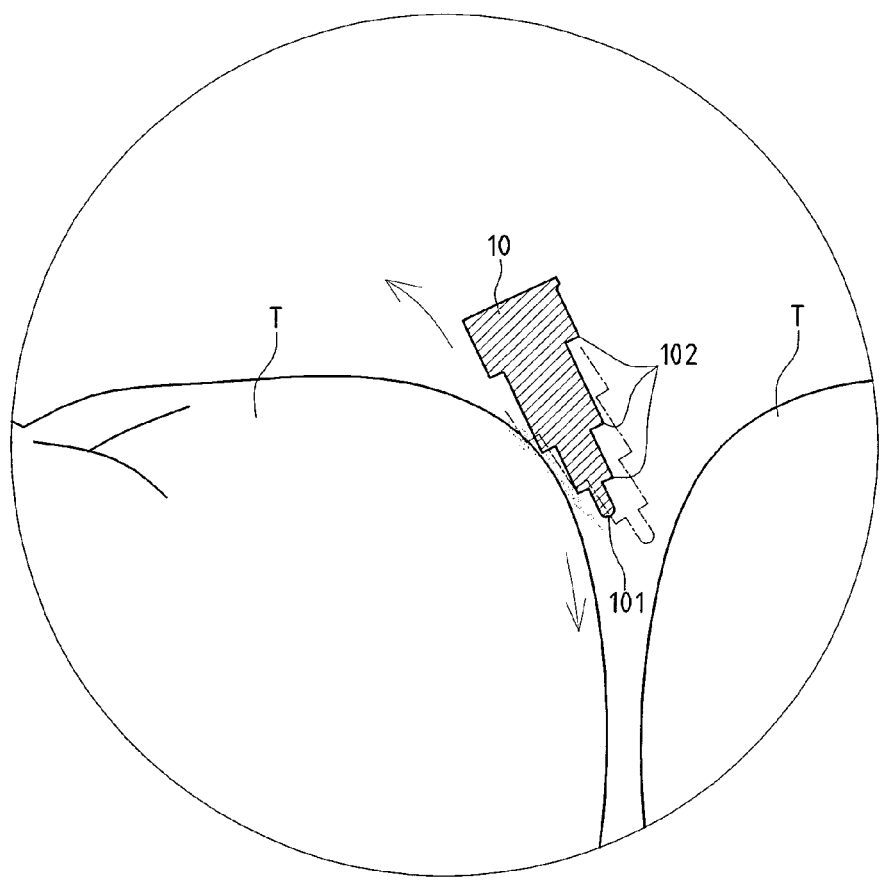
FIG. 9 is a schematic view illustrating use of the toothpick according to the present invention.

With reference to FIGS. 7-9, the toothpick structure according to the present invention includes a plurality of toothpicks 10 arranged in a row like a comb and is, thus, easy to carry. In use, one of the toothpicks 10 is separated from the toothpick structure, and the front end 101 of the separate toothpick 10 can be used to remove food residue between two teeth T. Furthermore, the separate toothpick 10 can be moved up and down, such that the at least one shoulder 102 on each side of each toothpick 10 can remove the food residue stuck on the surface of the teeth T.

Although specific embodiments have been illustrated and described, numerous modifications and variations are still possible without departing from the scope of the invention. The scope of the invention is limited by the accompanying claims.

The invention claimed is:

1. A method for manufacturing a comb-shaped toothpick structure, the method comprising:
    a first formation step including positioning a wooden block by a positioning device, moving the wooden block to a cutting position, and cutting the wooden block by a rotary cutter, with the rotary cutter including a plurality of dies on a surface thereof, with each of the plurality of dies including a top end having a blade, with each of the plurality of dies including two sides, with each of the two sides of each of the plurality of dies including an intermediate portion having at least one stepped cutting portion, with a cutter groove defined in a connection area between two adjacent dies, with the wooden block cut by the rotary cutter to form a plurality of toothpick shapes arranged in a row, with each of the plurality of toothpick shapes including a top edge formed by the cutter groove, with each of the plurality of toothpick shapes further including at least one stepped portion formed by the at least one stepped cutting portion, with each of the plurality of toothpick shapes further including a bottom, with the respective bottoms of the plurality of toothpick shapes connected to each other, and with a bottom groove located between two adjacent toothpick shapes and formed by the blade;
    a second formation step including partially cutting the plurality of toothpick shapes beginning from a start location spaced from an end of the plurality of toothpick shapes towards the end of the plurality of toothpick shapes, with the partial cutting in the second formation step carried out along a slope or a curve to cut two sides of the top edge, two sides of the at least one stepped portion, and two sides of the bottom groove of each of the plurality of toothpick shapes to form a front end of each of the plurality of toothpick shapes; and
    a cutting step including cutting the plurality of toothpick shapes from the wooden block along a cutting line to obtain the comb-shaped toothpick structure including a plurality of toothpicks, with a spacing between the top edge of each of the plurality of toothpick shapes and the cutting line being larger than a depth from the top edge of each of the plurality of toothpick shapes and the bottom grooves.

2. The method as claimed in claim 1, with the positioning device including a pressing rod and an actuation face, with the pressing rod controllable to position the wooden block on the actuation face, and with the actuation face moving the wooden block positioned thereon to the cutting position.

3. The method as claimed in claim 1, with the at least one stepped portion including first, second, and third stepped portions formed on of each of two sides of each of the plurality of toothpicks, with each of the first, second, and third stepped portions on one of the two sides of each of the plurality of toothpicks including a first lateral edge, with each of the first, second, and third stepped portions on another of the two sides of each of the plurality of toothpicks including a second lateral edge, with the first lateral edges of the first, second, and third stepped portions on the one of the two sides of each of the plurality of toothpicks located on a first plane, and with the second lateral edges of the first, second, and third stepped portions on the another of the two sides of each of the plurality of toothpicks located on a second plane.

4. The method as claimed in claim 3, with the partial cutting in the second formation step including using the rotary cutter to cut the two sides of the top edge, the two sides of the at least one stepped portion, and the two sides of the bottom groove of each of the plurality of toothpick shapes to form the front end of each of the plurality of toothpick shapes.

5. The method as claimed in claim 3, with each of the plurality of toothpicks including a longitudinal plane passing through the top edge and a central portion of the bottom, with an angle between the longitudinal plane and each of the first and second planes being in a range between 10° and 20°.

6. The method as claimed in claim 1, further comprising a polishing step before the cutting step, with the polishing step including controlling a polishing wheel to move along a path of the rotary cutter in the first and second formation steps to polish surfaces of the plurality of toothpick shapes after the first and second formation steps.

* * * * *